US008680298B2

(12) United States Patent
Bapuso et al.

(10) Patent No.: US 8,680,298 B2
(45) Date of Patent: Mar. 25, 2014

(54) PROCESS FOR THE PREPARATION OF ORLISTAT

(75) Inventors: Patil Dattatray Bapuso, Kolhapur (IN); Killol Patel, Junagadh (IN); Ashok Prasad, New Delhi (IN); Keshav Deo, Gurgaon (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 244 days.

(21) Appl. No.: 12/602,947

(22) PCT Filed: Jun. 6, 2008

(86) PCT No.: PCT/IB2008/052242
§ 371 (c)(1),
(2), (4) Date: Mar. 12, 2010

(87) PCT Pub. No.: WO2008/149321
PCT Pub. Date: Dec. 11, 2008

(65) Prior Publication Data
US 2010/0179335 A1 Jul. 15, 2010

(30) Foreign Application Priority Data

Jun. 6, 2007 (IN) .......................... 1223/DEL/2007

(51) Int. Cl.
*C07D 305/12* (2006.01)
(52) U.S. Cl.
USPC ...................................................... 549/328
(58) Field of Classification Search
USPC ...................................................... 549/328
See application file for complete search history.

(56) References Cited

U.S. PATENT DOCUMENTS

| 4,202,824 A | 5/1980 | Umezawa et al. | ... C07D 305/12 |
| 4,598,089 A | 7/1986 | Hadvary et al. | ...... C07D 305/12 |
| 4,874,558 A | 10/1989 | Fife et al. | ................ C07C 51/56 |
| 4,931,463 A | 6/1990 | Barbier et al. | ....... A61K 31/365 |
| 4,983,746 A | 1/1991 | Barbier et al. | ......... C07D 30/12 |
| 7,652,024 B2 * | 1/2010 | Bakshi et al. | ................. 514/278 |

FOREIGN PATENT DOCUMENTS

| IN | WO 2005005403 | * | 1/2005 | ........... C07D 301/12 |
| IN | WO 2007/039814 | * | 4/2007 | ........... C07D 301/12 |
| WO | WO 2005/005403 | | 1/2005 | ........... C07D 305/12 |
| WO | WO 2007/039814 | | 4/2007 | ........... C07D 305/12 |

OTHER PUBLICATIONS

Vlietstra: Recueil Oes Travaux Chimiques Oes Pays-Bas, vol. 101, No. 12, Jan. 1, 1982, pp. 460-462.*
Fieser, Mary: "Fieser and Fieser's Reagents for Organic Synthesis vol. 11" 1984, John Wiley &; Sons, ,New York, is a laboratory hand book for reagent, lists PFA for formylation reaction. XP002517590.*
Barbier, et al., "Synthesis of Tetrahydrolipstatin and Tetrahydroesterastin, Compound with a β-Lactone Moiety. Stereoselective Hydrogenation of a β-Keto δ-Lactone and Conversion of δ-Lactone in a β-Lactone", *Journal of Organic Chemistry*, 53:1218-1221(1988).
Fleming, et al.,"A Synthesis of (-)-Tetrahydrolipstatin in which the Relative Stereochemistry is Controlled by a Phenyldimethylsilyl Group", *Tetrahedron Letters*, 31(25):3645-3648 (1990).
Case-Greene, et al., "Asymmetric Synthesis of (-)-Tetrahydrolipstatin", *Synlett*, 11:781-782, (1991).
Chadha, et al., "Synthesis of Tetrahydrolipstatin", *Journal of Organic Chemistry*, 56:4714-4718 (1991).
Hanessian, et al. ,"Total Synthesis of (-)-Tetrahydrolipstatin", *Journal of Organic Chemistry*, 58:7768-7781 (1993).
Fleming, et al., Stereocontrol in Organic Synthesis Using Silicon-Containing Compounds. A Synthesis of (2)-tetrahydrolipstatin Using the Alkylation of a â-silyl Ester and the Hydroboration of an Allylsilane, *Journal of Organic Chemical Society, Perkins Trans*, 1(17):2679-2686 (1998).
Fieser, Mary, "Fieser and Fieser's Reagents for Organic Synthesis", John Wiley & Sons, New York, 11:567 (1984).
Vlietstra, et al., "Trimethylacetic Formic Anhydride. Improved Preparation and Use As A Highly Efficient and Selective N-formylating Reagent", *Recueil. Journal of the Royal Netherlands Chemical Society, Elsevier Science Publishers*, Amsterdam, NL, 101(12), p. 460-462 (1982).

* cited by examiner

*Primary Examiner* — Nizal Chandrakumar

(57) ABSTRACT

The present invention provides a process for preparing orlistat from amino orlistat using Pivaloyl Formic Anhydride (PFA) as an alkanoylating agent.

7 Claims, No Drawings

PROCESS FOR THE PREPARATION OF ORLISTAT

FIELD OF THE INVENTION

The present invention relates to improved processes for the preparation of orlistat, which is N-formyl-L-leucine derivative, in high purity.

BACKGROUND OF THE INVENTION

Orlistat, a tetrahydrolipstatin, is a useful pancreatic lipase-inhibiting agent and can be used for the prevention and treatment of obesity and hyperlipaemia. Chemically, orlistat is N-formyl-L-leucine [2S-[2alpha (R*), 3beta]]-1-[(3-hexyl-4-oxo-2-oxetanyl)methyl]dodecyl ester and is known from, for example, U.S. Pat. No. 4,598,089. It is represented by Formula I.

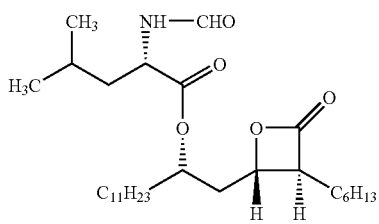

Formula I

Processes have previously been reported for the preparation of orlistat, such as in U.S. Pat. Nos. 4,202,824; 4,983,746; and 4,931,463; *J. Org. Chem.*, 53, (1988), 1218-1221; *Tetrahedron Lett.*, 31, (1990), 3645-3648; *Synlett.*, 11, (1991), 781-782; *J. Org. Chem.*, 56, (1991), 4714-4718; *J. Org. Chem.*, 58, (1993), 7768-7781; and *J. Chem. Soc., Perkin Trans.* 1, 17, (1998), 2679-2686.

U.S. Pat. No. 4,931,463 and WO 2005/005403 discloses the use of formic acid anhydride, acetic acid anhydride or a mixed acid anhydride such as formic acid/acetic acid anhydride for alkanoylating (S)-leucine (S)-1-[[(2S,3S)-3-hexyl-4-oxo-2-oxetanyl]methyl dodecyl ester (amino orlistat) of Formula II.

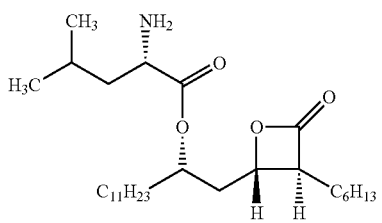

Formula II to produce orlistat.

It has been observed that there are certain disadvantages in using acetic anhydride and the mixed anhydride of formic acid/acetic acid anhydride as alkanoylating agents. In particular, formic acid/acetic acid anhydride used as alkanoylating agent leads to the formation of a by-product of Formula (III)

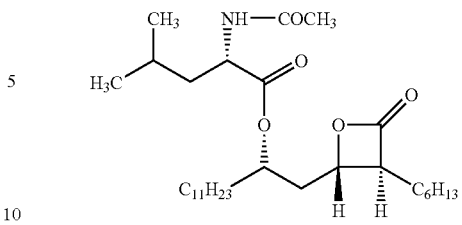

Formula (III)

which is chemically N-(acetyl)-L-leucine (1S)-1-[[(2S,3S)-3-hexyl-4-oxo-2-oxetanyl]methyl]dodecyl ester (deformyl-N-acetyl orlistat).

Therefore, there has been an ongoing research for new alkanoylating agents, which are capable of introducing the formyl group in good yield without producing by-products.

In their endeavor to find a simple, efficient, cost-effective process for the manufacture of orlistat in high yield and purity, the present inventors have found that the selection of alkanoylating agent during alkanoylation of amino orlistat influences the amount of by-products formed.

SUMMARY OF THE INVENTION

Accordingly, the present invention provides improved processes for the preparation of orlistat of Formula (I)

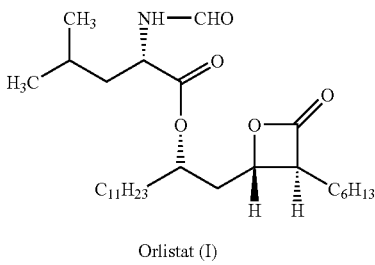

Orlistat (I)

comprising alkanoylating (S)-leucine (S)-1-[[(2S,3S)-3-hexyl-4-oxo-2-oxetanyl]methyl dodecyl ester (amino orlistat) of Formula (II),

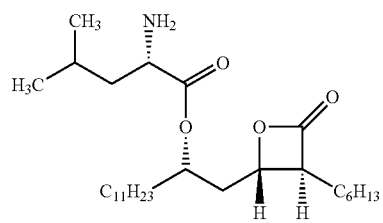

Formula II with Pivaloyl Formic Anhydride (PFA), to give orlistat of Formula (I)

DETAILED DESCRIPTION OF THE INVENTION

Amino orlistat may be obtained by methods known in the art including, for example, U.S. Pat. Nos. 4,598,089; 4,983,746; and 4,931,463 and WO 2005/005403, which are incorporated herein by reference.

Amino orlistat may be obtained as a solution directly from a reaction mixture of the last step of a process in which it is prepared and used as such for the preparation of orlistat.

In general, amino orlistat may be obtained by deprotecting a protected amino orlistat.

The Pivaloyl Formic Anhydride may be obtained by reacting formic acid with pivaloyl chloride in a suitable solvent and in the presence of a base.

The base may be an organic or inorganic base. Examples of organic base include, for example, trimethylamine, triethylamine, tributylamine, triisopropylamine, diisopropylethylamine, pyridine, morpholine, DBU (1,8-diazabicyclo-[5.4.0]-undec-7-ene), DBN (1,5-diazabicyclo-[4.3.0]-non-5-ene), 4-dimethylamino pyridine and mixtures thereof. Examples of inorganic base include, for example, alkali metal carbonate, bicarbonate, hydroxide and mixtures thereof. Examples of alkali metal carbonate include lithium carbonate, sodium carbonate and potassium carbonate. Examples of alkali metal bicarbonate include sodium bicarbonate and potassium bicarbonate. Examples of alkali metal hydroxide include sodium hydroxide and potassium hydroxide.

Examples of solvent include ethers, such as dioxane and tetrahydrofuran, and chlorinated hydrocarbons, such as methylenedichloride and ethylenedichloride.

The addition of pivaloyl chloride may be carried out at a temperature range from about 0° C. to about −20° C.

The reaction of formic acid with pivaloyl chloride may be carried out at a temperature range from about 0° C. to about −20° C. for a period of about 30 minutes to about 3 hours.

The alkanoylation of amino orlistat may be carried out in a suitable solvent, for example, ethers, such as dioxane and tetrahydrofuran, and chlorinated hydrocarbons, such as methylenedichloride and ethylenedichloride.

The alkanoylation reaction of amino orlistat may be carried out at a temperature range from about −10° C. to about 10° C.

The reaction mixture can be quenched by water and extracted with suitable solvent.

The quenching of reaction may be carried out at a temperature range from about −5° C. to about 30° C., for example, from about −5° C. to about 0° C.

Orlistat obtained may be recrystallized from a suitable solvent or mixture to obtain pure orlistat.

The solvents which can be used for the crystallization of orlistat include aliphatic hydrocarbons. Examples of aliphatic hydrocarbon include hexane, pentane, heptane, cyclohexane or mixtures thereof.

The crystallization may be performed at temperature of from about 0° C. to about 25° C. for a period of about 30 minutes to about 3 hours.

Orlistat obtained by the present processes is substantially free of the by-product of Formula (III). This believed to be the case as the formation of this by-product is not possible, as acetic anhydride or acetic acid anhydride/formic acid anhydride mixtures are not employed, according to the present invention.

In the following section, preferred embodiments are described by way of examples to illustrate the process. However, these are not intended in any way to limit the scope of the claims. Several variants of these examples would be evident to persons ordinarily skilled in the art.

EXAMPLES

Example 1

Preparation of (S)-leucine (S)-1-[[(2S,3S)-3-hexyl-4-oxo-2-oxetanyl]methyl dodecyl ester (amino orlistat)

A solution of (S)—N-[(benzyloxy)carbonyl]leucine (S)-1-[[(2S,3S)-3-hexyl-4-oxo-2-oxetanyl]methyl]dodecyl ester (100 g, 0.1663 mol) in dichloromethane (300 mL) was hydrogenated in the presence of 10% palladium carbon (4.0 g, 50% moisture) at 25° C. to 30° C. under hydrogen atmosphere (2.5 to 3.0 Kg) for 1.5 hours. After completion of the reaction, the reaction mixture was filtered through a hyflow bed and the hyflow bed was washed with dichloromethane (200 mL). The filtrate so obtained was used directly in Example 3.

Example 2

Preparation of Pivaloyl Formic Anhydride (PFA)

To a stirred mixture of formic acid (38 g) and triethylamine (46 g) in dichloromethane (500 ml) at −10° C., pivaloyl chloride (50 g) was added dropwise, while maintaining a temperature of −10 to −5° C. This reaction mixture was stirred for an additional two hours at −10 to −5° C. to ensure the complete conversion of pivaloyl chloride to pivaloyl formic anhydride (PFA). This stock solution of PFA was used in its entirety for the formylation of amino orlistat to orlistat.

Example 3

Preparation of (S)—N-formyl leucine (S)-1-[[(2S, 3S)-3-hexyl-4-oxo-2-oxetanyl]methyl dodecyl ester (orlistat)

To the stirred dichloromethane solution of amino orlistat product of Example 1, the stock solution of pivaloyl formic anhydride from Example 2 was added at −5 to −10° C. and the temperature was maintained for 1 hour further to ensure complete consumption of amino orlistat. Reaction mass was quenched in DI water (1.0 lit) and dichloromethane was recovered. The resultant residue was dissolved in hexane (800 ml) and sequentially washed with aqueous sodium bicarbonate as well as DI water. The separated hexane layer was treated with carbon and silica gel and filtered over celite. The filtrate was cooled to 0 to −5° C. to get solid. This solid was filtered under vacuum and kept under suction. This wet solid (150 g) was dissolved in hexane (1000) and was cooled to 0 to 5° C. to get crude orlistat, which was dried at 25-30° C. under vacuum.

HPLC purity: 98.73%

Yield: 120 g (wet)

Example 4

Preparation of Pure Orlistat

Orlistat crude (120 g, wet) was dissolved in n-hexane (1000 ml) and resulting n-hexane solution was cooled at 0 to 5° C. over a period of 4-6 hours. Temperature was maintained at 0 to 5° C. for further 6-7 hours and the resulting solid was filtered at 0 to 5° C. and dried at 30-35° C. under reduced pressure.

Yield: 68 gm

By-product of Formula (III): Not detected (upper limit of any known and unknown impurities is NMT 0.15%).

HPLC purity: 99.55%

We claim:
1. A process for preparation of orlistat of Formula (I)

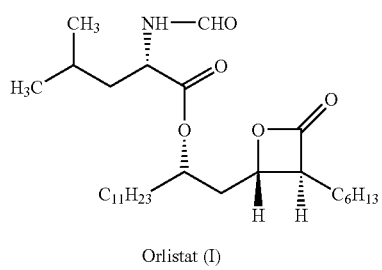

Orlistat (I)

comprising
 a) reacting formic acid with pivaloyl chloride in the presence of a base in a suitable solvent to prepare a stock solution of Pivaloyl Formic Anhydride (PFA);
 b) alkanoylating (S)-leucine (S)-1-[[(2S,3S)-3-hexyl-4-oxo-2-oxetanyl]methyl dodecyl ester (amino orlistat) of Formula (II),

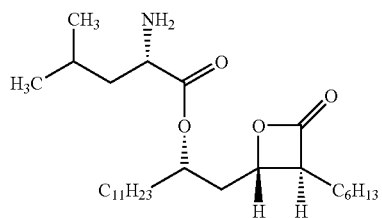

Formula II with the stock solution prepared in step a), to give orlistat of Formula (I) which is substantially free from by-product of Formula III

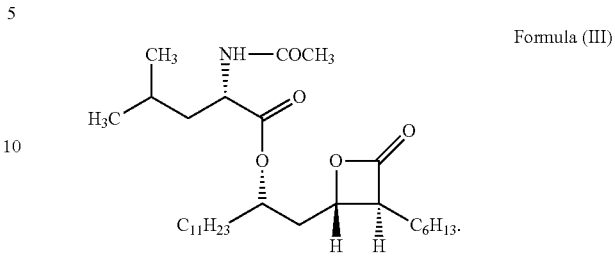

Formula (III)

2. The process according to claim 1, wherein amino orlistat is obtained as a solution directly from a reaction mixture of the last step of a process in which it is prepared.

3. The process according to claim 1, wherein amino orlistat is obtained by deprotecting protected amino orlistat.

4. The process according to claim 1, wherein the reaction of formic acid with pivaloyl chloride in step a) is carried out at a temperature range from about 0° C. to about −20° C. for a period of about 30 minutes to 3 hours.

5. The process according to claim 1, wherein alkanoylation reaction in step b) is carried out at a temperature range from about −10° C. to about 0° C.

6. The process according to claim 1, wherein obtained orlistat is recrystallized with aliphatic hydrocarbon selected from the group comprising of hexane, pentane, heptane, cyclohexane and mixtures thereof.

7. The process according to claim 6, wherein the crystallization is performed at temperature of from about 0° C. to about 25° C. for a period of 30 minutes to about 3 hours.

* * * * *

UNITED STATES PATENT AND TRADEMARK OFFICE
CERTIFICATE OF CORRECTION

PATENT NO. : 8,680,298 B2  
APPLICATION NO. : 12/602947  
DATED : March 25, 2014  
INVENTOR(S) : Patil Dattatray Bapuso et al.

Page 1 of 1

It is certified that error appears in the above-identified patent and that said Letters Patent is hereby corrected as shown below:

ON THE TITLE PAGE, (56) REFERENCES CITED:

For U.S. Patent Documents:

"4,983,746 A   1/1991   Barbier et al.  ...... C07D 30/12"

should read:

-- 4,983,746 A   1/1991 Barbier et al.  ...... C07D 305/12 --

For Foreign Patent Documents:

"IN   WO 2005005403   * 1/2005   ....... C07D 301/12  
IN   WO 2007/039814   * 4/2007   ....... C07D 301/12"

should read:

-- WO   WO 2005/005403   * 1/2005   ....... C07D 301/12  
WO   WO 2007/039814   * 4/2007   ....... C07D 301/12 --

Signed and Sealed this  
Twenty-seventh Day of January, 2015

Michelle K. Lee  
*Deputy Director of the United States Patent and Trademark Office*